(12) United States Patent
Li et al.

(10) Patent No.: US 11,246,888 B2
(45) Date of Patent: Feb. 15, 2022

(54) SLIT2D2-CHIMERIC ANTIGEN RECEPTOR AND APPLICATION THEREOF

(71) Applicant: Asclepius (Suzhou) Technology Company Group Co., Ltd., Suzhou (CN)

(72) Inventors: Huashun Li, Suzhou (CN); Baolei Wang, Suzhou (CN); Baoyong Ren, Suzhou (CN)

(73) Assignee: ASCLEPIUS (SUZHOU) TECHNOLOGY COMPANY GROUP CO., LTD., Suzhou (CN)

( * ) Notice: Subject to any disclaimer, the term of this patent is extended or adjusted under 35 U.S.C. 154(b) by 559 days.

(21) Appl. No.: 16/160,735

(22) Filed: Oct. 15, 2018

(65) Prior Publication Data
US 2019/0231819 A1    Aug. 1, 2019

Related U.S. Application Data

(63) Continuation of application No. PCT/CN2016/102374, filed on Oct. 18, 2016.

(30) Foreign Application Priority Data

Apr. 15, 2016 (CN) .......................... 201610235109.2

(51) Int. Cl.
*A61K 35/17* (2015.01)
*C07K 14/705* (2006.01)
(Continued)

(52) U.S. Cl.
CPC .............. *A61K 35/17* (2013.01); *A61P 35/00* (2018.01); *C07K 14/705* (2013.01);
(Continued)

(58) Field of Classification Search
CPC .. C07K 2319/74; C07K 14/705; C07K 16/28; C07K 14/70503; C07K 2319/70;
(Continued)

(56) References Cited

U.S. PATENT DOCUMENTS

| 9,868,774 B2 * | 1/2018 | Orentas ................... A61P 35/00 |
| 10,266,580 B2 * | 4/2019 | Scholler ............ C07K 14/70517 |
| 10,526,406 B2 * | 1/2020 | Duchateau ....... C07K 14/70578 |

FOREIGN PATENT DOCUMENTS

| CN | 104829733 A | 8/2015 |
| CN | 105431532 A | 3/2016 |

(Continued)

OTHER PUBLICATIONS

O'Hear, C., et al. (2015). Anti-CD33 chimeric antigen receptor targeting of acute myeloid leukemia. Haematologica, 100(3), 336. (Year: 2015).*

(Continued)

*Primary Examiner* — Kevin K Hill
*Assistant Examiner* — Anjeanette Roberts
(74) *Attorney, Agent, or Firm* — Flener IP & Business Law; Zareefa B. Flener

(57) ABSTRACT

A chimeric antigen receptor (CAR) and a gene encoding the CAR. The CAR comprises an extracellular domain capable of binding to an antigen, a transmembrane domain, and intracellular immune co-stimulatory molecule, wherein the extracellular domain comprises a D2 domain of a Slit2 protein. A chimeric antibody-expressing cell, which introduces a gene encoding the CAR into a cell so as to express the CAR on the surface of the cell. The CAR or CAR-expressing cell can be used as a cell drug for the treatment of tumor diseases. By using the CAR for engineering cells, (Continued)

especially T cells, the engineered T cells can specifically recognize and kill tumors, and have higher tumoricidal activity.

8 Claims, 6 Drawing Sheets

Specification includes a Sequence Listing.

(51) Int. Cl.
| | |
|---|---|
| *C07K 19/00* | (2006.01) |
| *C12N 15/09* | (2006.01) |
| *A61P 35/00* | (2006.01) |
| *C07K 14/725* | (2006.01) |
| *C12N 15/85* | (2006.01) |
| *C12N 5/10* | (2006.01) |
| *C07K 14/78* | (2006.01) |
| *C07K 14/73* | (2006.01) |

(52) U.S. Cl.
CPC .... *C07K 14/7051* (2013.01); *C07K 14/70514* (2013.01); *C07K 14/70517* (2013.01); *C07K 14/70575* (2013.01); *C07K 14/78* (2013.01); *C07K 19/00* (2013.01); *C12N 5/10* (2013.01); *C12N 15/09* (2013.01); *C12N 15/85* (2013.01)

(58) Field of Classification Search
CPC ............... C07K 19/00; C07K 2317/21; C07K 16/2863; C07K 14/47; C07K 14/7051; C07K 2319/03; C07K 2317/622; C07K 2319/00; C07K 2319/33; C07K 16/2803; C07K 14/70514; C07K 14/70517; C07K 14/70575; C07K 14/78; A61K 35/17; A61P 35/00; C12N 5/10; C12N 15/09; C12N 15/85

See application file for complete search history.

(56) References Cited

FOREIGN PATENT DOCUMENTS

| GN | 104119445 A | 10/2014 |
|---|---|---|
| GN | 104119447 A | 10/2014 |
| GN | 104126009 A | 10/2014 |
| WO | WO2013126720 A2 | 8/2013 |
| WO | WO2014180306 A1 | 11/2014 |
| WO | WO2015092024 A2 | 6/2015 |

OTHER PUBLICATIONS

Morlot, C., Thielens, N. M., Ravelli, R. B., Hemrika, W., Romijn, R. A., Gros, P., . . . & McCarthy, A. A. (2007). Structural insights into the Slit-Robo complex. Proceedings of the National Academy of Sciences, 104(38), 14923-14928. (Year: 2007).*

Chang, P. H., et al. (2012). Activation of Robo1 signaling of breast cancer cells by Slit2 from stromal fibroblast restrains tumorigenesis via blocking PI3K/Akt/β-catenin pathway. Cancer research, 72(18), 4652-4661. (Year: 2012).*

Abate-Daga D, Davila ML. CAR models: next-generation CAR modifications for enhanced T-cell function. Molecular Therapy-Oncolytics. Jan. 1, 2016;3:16014. (Year: 2016).*

Pameijer CR, Navanjo A, Meechoovet B, Wagner JR, Aguilar B, Wright CL, Chang WC, Brown CE, Jensen MC. Conversion of a tumor-binding peptide identified by phage display to a functional chimeric T cell antigen receptor. Cancer gene therapy. Jan. 2007; 14(1):91-7. (Year: 2007).*

Alignments of SEQ ID No. 5 with closest prior art sequences cited in office action; see results 2 and 6 (highlighted). (Year: 2021).*

Written Opinion of the International Searching Authority for PCT/CN2016/102374 dated Jan. 5, 2017.

Slit2 involvement in glioma cell migration is mediated by Robo1 receptor Published online: Oct. 30, 2007.

Slit2Robo1 signaling promotes intestinal tumorigenesis through Src-mediated activation of the Wntβ-catenin pathway Published online: Dec. 18, 2014.

Structural insights into the Slit-Robo complex Edited by Corey S. Goodman, Renovis, South San Francisco, CA, and approved Aug. 7, 2007. Sep. 18, 2007 vol. 104 No. 38 14923-14928.

China National Intellectual Property Administration, First Office Action, App. No 201610235109.2, Applicant: Asclepius (Suzhou) Technology Company Group Co., dated Apr. 27, 2020.

Morlot, C., et al., Title: Chain B, Complex Between the Second Lrr Domain of Sli2 and the First Ig Domain from Robo1, Published: Oct. 10, 2012.

* cited by examiner

SLIT2D2-CHIMERIC ANTIGEN RECEPTOR AND APPLICATION THEREOF

CROSS-REFERENCE TO RELATED APPLICATION

This application is a continuation application of International patent application No. PCT/CN2016/102374, filed on Oct. 18, 2016, which claims the benefit and priority of Chinese patent application No. CN201610235109.2, filed on Apr. 15, 2016, each of which is incorporated herein by reference in its entirety and for all purposes.

FIELD OF THE INVENTION

The present invention relates to the field of tumor therapeutic drugs, in particular to the use of a Slit2D2-chimeric antigen receptor in a medicament for preventing and/or treating a tumor highly expressing Robo1.

BACKGROUND OF THE INVENTION

Human T lymphocytes recognize target cells through T cell receptors on their surface, and this recognition is specific, that is, a certain T lymphocyte recognizes only a target cell having a specific antigen, and this specific antigen is presented to the T lymphocyte under the action of a specific molecule after being processed inside the cell. Such molecule with antigen presentation function is either present on the surface of an antigen-presenting cell or present on the surface of a target cell. There are at least two factors that cause T lymphocytes in the body to fail to well recognize cancer cells: (1) cancer cells down-regulate the expression of the antigen-presenting molecules, and (2) the presented antigens have weak affinity for T-cell receptors. Although cancer patients have highly specific T lymphocytes in their bodies, the number of these cells is too small to treat cancer. Based on this situation, scientists have proposed the concept of constructing a chimeric T cell receptor (now commonly referred to as a chimeric antigen receptor). The chimeric antigen receptor (CAR) mainly consists of two parts, one end is located outside the cell and can specifically recognize a certain antigen on the surface of a cancer cell, and the other end is located in the cell and contains a signal-activating element (such as the Zeta chain of a T cell receptor) and acts to transmit the signal to activate the T cells. Such CAR-expressing T lymphocytes (CART cells) can avoid the limitation of T cell receptors to recognize target cells, thereby playing a role in targeting cancer cells.

Currently, clinical trials of CART therapy are growing rapidly, most of which are assessments of the treatment of B-cell malignancies. Most B-cell malignancies and normal B cells express CD19 antigen, but other types of cells do not have CD19, therefore, the CD19 is a good therapeutic target. The CD19 CART cells used in different clinical trials have some differences in composition and clinical design, but all have reported significant effects, which can achieve a response rate of 60-90% for treatment of relapsed or refractory lymphocytic leukemia, and some patients achieve sustained remission, up to 2 years. Although it is unknown that how long the CD19 CART therapy can achieve sustained relief, it is certain that this immunotherapy has brought previously unreachable results to some patients.

In addition to blood system tumors, researchers have been working to extend CART therapy to solid tumors. Clinical trials have shown that GD2-specific CART has a certain effect on neuroblastoma, while no therapeutic effect is shown by aFR-specific CART cells against ovarian cancer, CAIX-specific CART cells against renal cell carcinoma, or PSMA-specific CART cells against prostate cancer. Carl H June et al. of the University of Pennsylvania reported the results of treating refractory and metastatic pancreatic ductal adenocarcinoma with mesothelin-specific CART cells at the 2015 American Society of Clinical Oncology. The results showed that the patients were well tolerated by CART cells, did not have cytokine syndrome, and the CART cells could be detected in the peripheral blood for a short period of time, and two patients recovered to a stable condition. Therefore, treatment of solid tumors by CART is still in its early stage, and there are still many problems to be solved.

Robo1 is a potential new target for treating solid tumors. Robo is a transmembrane receptor protein. In mammals, four Robo genes have been cloned. From the perspective of species evolution, the extracellular portion of Robo1, 2, and 3 are very conserved, which consist of five Ig-like functional regions and three Fibronectin type III repeats ranging from fruit flies to humans. Robo has a short transmembrane domain and a longer intracellular domain; and according to the sequence conservation, the intracellular domain is divided into four smaller domains, individually named: CC0, CC1, CC2, and CC3. The structure of Robo4 is quite different from that of the other three family members. The extracellular structure of Robo4 has only two Ig-like functional domains and three Fibronectin type III repeats; and its intracellular structure has only two domains, CC0 and CC2 The extracellular IgG domains of Robos are considered necessary for binding to the ligand Slit, and the longer intracellular domain interacts with some important signaling molecules to participate in downstream signal transduction of Slit/Robo, thereby completing the transmission of the stimulation signal from the outside of the cell to the internal skeleton. At present, the structural analysis of the protein in the interaction region between Slit2 and Robo has been completed, and it is found that the second domain D2 of Slit2 binds to Ig1 of Robo1, thereby initiating signal transduction. The analysis of the tertiary structure of Slit2/Robo1 interaction region is shown in FIG. 1.

Histopathological examination reveals that Robo1 is overexpressed in various cancers, such as hepatocellular carcinoma, breast cancer, colon cancer, pancreatic cancer, prostate cancer, glioma, and the like. The study by Ito et al. showed that Robo1 was abundantly expressed in liver cancer, and expressed only in a small amount in normal tissues, and 84.7% of liver cancer tissue samples had positive expression; therefore, Robo1 can be used as a new hepatocellular tumor-associated antigen and is a potential therapeutic and diagnostic target. The detection results by GRÖNE et al. showed that 80% of colon cancer patients had high expression of Robo1 mRNA in cancer tissues, and in 45% of patients, the expression of Robo1 mRNA in cancer tissues was four times that in normal tissues, and in 15% of patients, the expression of Robo1 mRNA in cancer tissues was 12 times that in normal tissues, therefore, Robo1 can provide a potential target for the treatment of colon cancer. By comparing pancreatic ductal carcinoma with benign tissue around it, He et al. found that the expression of Robo1 was up-regulated in cancer tissues, and this up-regulation may be associated with lymphatic metastasis in pancreatic cancer cells. The study by Huang et al. also showed that Robo1 was involved in the migration of colon cancer. From the analysis in the database XenoBase (see FIG. 2), it is shown that Robo1 protein molecule is highly expressed in most tumor cells. From the analysis in the database GeneCards (see FIG. 3), it is shown that Robo1 molecule is underexpressed or not expressed in normal tissues, suggesting that Robo1 is a potential new target for tumor therapy.

The present invention develops a CAR targeting the Robo1 antigen molecule, which is expressed in a cell and can be used for the treatment of a tumor highly expressing Robo1.

SUMMARY OF THE INVENTION

One object of the present invention is to provide a CAR for preventing and/or treating a tumor highly expressing Robo1.

Another object of the present invention is to provide a CAR-expressing cell for preventing and/or treating a tumor highly expressing Robo1.

Still another object of the present invention is to provide a medicament for preventing and/or treating a tumor highly expressing Robo1.

Accordingly, a first aspect of the present invention provides a CAR comprising an extracellular domain capable of binding to an antigen, a transmembrane domain, and an intracellular immune costimulatory molecule, wherein the extracellular domain comprises a D2 domain of a Slit2 protein.

The D2 domain of Slit2 protein of the present invention, referred to as Slit2D2, has:

1) an amino acid sequence as shown in SEQ ID NO: 1, or
2) an amino acid sequence derived from 1) by substitution and/or deletion and/or addition of one or several amino acid residues and having the same function.

Preferably, the CAR consists of the D2 domain of Slit2 protein, the transmembrane domain, and the intracellular immune costimulatory molecule in turn.

Preferably, the transmembrane domain comprises one or more of CD28, CDR, CD45, CD4, CD5, CD8, CD9, CD16, CD22, CD33, CD37, CD134, CD137, ICOS, and CD154 transmembrane domains.

Preferably, the transmembrane domain is CD8 transmembrane domain.

The CD8 transmembrane domain of the present invention has:

3) an amino acid sequence as shown in SEQ ID NO: 2, or
4) an amino acid sequence derived from 3) by substitution and/or deletion and/or addition of one or several amino acid residues and having the same function.

Preferably, the intracellular immune costimulatory molecule comprises one or more of CD3ζ, CD3γ, CD3δ, CDRε, CD5, CD22, CD79a, CD79b, CD66d, CD2, CD4, CD5, CD28, CD134, CD137, ICOS, CD154, 4-1BB and OX40 intracellular domains.

Preferably, the intracellular immune costimulatory molecule consists of 4-1BB and CD3ζ intracellular domains.

The 4-1BB intracellular domain of the present invention has:

5) an amino acid sequence as shown in SEQ ID NO: 3, or
6) an amino acid sequence derived from 5) by substitution and/or deletion and/or addition of one or several amino acid residues and having the same function; and the CD3ζ intracellular domain of the present invention has:

7) an amino acid sequence as shown in SEQ ID NO: 4, or
8) an amino acid sequence derived from 7) by substitution and/or deletion and/or addition of one or several amino acid residues and having the same function.

Preferably, the CAR of the present invention consists of the D2 domain of Slit2 protein, CD8 transmembrane domain, 4-1BB intracellular domain, and CD3ζ intracellular domain, referred to as Slit2D2-CD8-TM-4-1BB-CD3ζ, also known as Slit2D2-CAR.

The Slit2D2-CD8-TM-4-1BB-CD3ζ of the present invention has:

9) an amino acid sequence as shown in SEQ ID NO: 5, or
10) an amino acid sequence derived from 9) by substitution and/or deletion and/or addition of one or several amino acid residues and having the same function.

Preferably, in the CAR, the substitution and/or deletion and/or addition of the one or several amino acid residues is a substitution and/or deletion and/or addition of no more than 10 amino acid residues.

The D2 domain of Slit2 protein of the present invention is directly linked to the N-terminal of the CD8 transmembrane domain via its C-terminal, or the D2 domain of Slit2 protein is directly linked to the C-terminal of the CD8 transmembrane domain via its N-terminal, i.e., the D2 domain of Slit2 protein is directly linked to the CD8 transmembrane domain without any linker peptide in between.

The present invention also provides a gene encoding the CAR of the present invention, and the CAR comprises an extracellular domain capable of binding to an antigen, a transmembrane domain, and an intracellular immune costimulatory molecule, wherein the extracellular domain comprises a D2 domain of Slit2 protein. The D2 domain of Slit2 protein of the present invention, referred to as Slit2D2, has a gene sequence as shown in SEQ ID NO: 6.

Preferably, the CAR of the present invention consists of the D2 domain of Slit2 protein, CD8 transmembrane domain, 4-1BB intracellular domain, and CD3 intracellular domain, referred to as Slit2D2-CD8-TM-4-1BB-CD3, wherein, the gene of the D2 domain of Slit2 protein has a sequence as shown in SEQ ID NO: 6, the gene of the CD8 transmembrane domain has a sequence as shown in SEQ ID NO: 7, the gene of the 4-1BB intracellular domain has a sequence as shown in SEQ ID NO: 8, and the gene of the CD3ζ intracellular domain has a sequence as shown in SEQ ID NO: 9.

The gene of the Slit2D2-CD8-TM-4-1BB-CD3ζ of the present invention has a sequence as shown in SEQ ID NO: 10;

Or, is a DNA molecule hybridizing with the sequence as shown in SEQ ID NO: 10 under stringent conditions and encoding a related protein for preventing and/or treating a tumor;

Or, is a DNA molecule having at least 90% or more, preferably 95% or more, and more preferably 98% or more homology to the sequence as shown in SEQ ID NO: 10 and encoding a related protein for preventing and/or treating a tumor.

The present invention also provides a biological material related to the CAR, comprising a recombinant vector, an expression cassette, a recombinant cell, a recombinant strain, and a recombinant virus which contain the gene encoding the CAR of the present invention. Preferably, the recombinant vector of the present invention is a recombinant expression vector or a recombinant cloning vector.

The CAR of the present invention can be artificially synthesized, or can be obtained by first synthesizing the coding gene thereof and then performing biological expression. In the present invention, the coding gene may be synthesized by a conventional method. A base sequence encoding a specified CAR may be easily prepared from the amino acid sequence of the CAR. The nucleic acid of the present invention may be prepared by obtaining a base sequence encoding an amino acid sequence from the NCBI Ref Seq ID or GenBenk accession number of the amino acid sequence, and employing standard molecular biological and/or chemical procedures. For example, the nucleic acid of the present invention may be prepared by synthesizing a nucleic acid according to a base sequence and performing polymerase chain reaction (PCR) of a DNA fragment obtained from a cDNA database A second aspect of the present invention provides a CAR-expressing cell, and the CAR-expressing cell is a cell which a gene encoding the CAR of the present invention is introduced into.

In the present invention, the cell may be a cell derived from a mammal (for example, human, mouse, rat, monkey), which is collected, isolated, purified or induced from body fluid, tissue or organ such as blood (peripheral blood, umbilical cord blood, etc.) or bone marrow. Preferably, the cell is a T cell or a cell population containing T cells (for example, PBMC), and more preferably, the T cell is a T cell derived from human peripheral blood.

Preferably, the CAR is Slit2D2-CD8-TM-4-1BB-CD3ζ, which is referred to as Slit2D2-CAR, wherein the gene of the Slit2D2-CD8-TM-4-1BB-CD3ζ has a sequence as shown in SEQ ID NO: 10;

Or, is a DNA molecule hybridizing with the sequence as shown in SEQ ID NO: 10 under stringent conditions and encoding a related protein for preventing and/or treating a tumor;

Or, is a DNA molecule having at least 90% or more, preferably 95% or more, and more preferably 98% or more homology to the sequence as shown in SEQ ID NO: 10 and encoding a related protein for preventing and/or treating a tumor.

Preferably, the CAR-expressing cell is a T cell into which the gene encoding the Slit2D2-CD8-TM-4-1BB-CD3ζ is introduced, and is referred to as Slit2D2-CART.

The present invention also provides a method for preparing a CAR-expressing cell including the step of introducing a gene encoding the CAR of the present invention into a cell.

In the present invention, introducing a gene encoding the CAR into a cell specifically includes the following steps:

Synthesizing and amplifying the gene encoding the CAR, and cloning the gene into an expression vector;

Transfecting the cell with a packaging plasmid and the expression vector; and

Allowing the cell to express the CAR, wherein the Slit2D2 molecule is expressed on the cell surface.

In the present invention, the cell may be a cell derived from a mammal (for example, human, mouse, rat, monkey), which is collected, isolated, purified or induced from body fluid, tissue or organ such as blood (peripheral blood, umbilical cord blood, etc.) or bone marrow. Preferably, the cell is a T cell or a cell population containing T cells (for example, PBMC), and more preferably, the T cell is a T cell derived from human peripheral blood.

In the present invention, the expression vector may adopt a viral vector such as a retroviral vector (including a carcinogenic retrovirus vector, a lentiviral vector, and a pseudotype vector), an adenovirus vector, a vaccinia virus vector or an HSV vector which lacks replication ability and is unable to self-replicate in the transfected cells. In the present invention, a wide variety of commercially available packaging plasmids for packaging retroviral vectors may be selected according to the retroviruses, and retrovirus particles may also be prepared using 293 cells or 293T cells having high transfection efficiency.

Preferably, the CAR is Slit2D2-CD8-TM-4-1BB-CD3ζ, which is referred to as Slit2D2-CAR, wherein the gene of the Slit2D2-CD8-TM-4-1BB-CD3ζ has a sequence as shown in SEQ ID NO: 10;

Or, is a DNA molecule hybridizing with the sequence as shown in SEQ ID NO: 10 under stringent conditions and encoding a related protein for preventing and/or treating a tumor;

Or, is a DNA molecule having at least 90% or more, preferably 95% or more, and more preferably 98% or more homology to the sequence as shown in SEQ ID NO: 10 and encoding a related protein for preventing and/or treating a tumor.

Preferably, the method for preparing a CAR-expressing cell includes the step of introducing a gene encoding Slit2D2-CD8-TM-4-1BB-CD3ζ into a T cell.

In a specific embodiment of the present invention, the method for preparing a CAR-expressing cell specifically includes the following steps:

Synthesizing and amplifying a gene of Slit2D2-CD8-TM-4-1BB-CD3ζ having a sequence as shown in SEQ ID NO: 10, and cloning the gene into a lentiviral expression vector;

Transfecting a 293T cell with a lentiviral packaging plasmid and the lentiviral expression vector, packaging and preparing a lentivirus; and Isolating a human peripheral blood T cell, culturing and expanding, transfecting the T cell with the lentivirus, allowing the T cell to express the Slit2D2-CD8-TM-4-1BB-CD3ζ, wherein, the Slit2D2 molecule is expressed on the surface of the T cell, and a T cell activation signal is transmitted intracellularly by the 4-1BB-CD3ζ molecule.

A third aspect of the present invention provides a pharmaceutical composition comprising the CAR of the present invention or the CAR-expressing cell of the present invention and a pharmaceutically acceptable excipient.

The pharmaceutical composition of the present invention may be tablets (including sugar-coated tablets, film-coated tablets, sublingual tablets, orally disintegrating tablets, oral tablets, etc.), pills, powder, granules, capsules (including soft capsules, microcapsules), pastilles, syrups, liquids, emulsions, suspensions, controlled release preparations (for example, transient release preparations, sustained release preparations, sustained release microcapsules), aerosols, film agents (for example, oral disintegrating film agents, oral mucosa-adhesive film agents), injections (for example, subcutaneous injections, intravenous injections, intramuscular injections, intraperitoneal injections), intravenous drips, transdermal absorption preparations, ointments, lotions, adhesive preparations, suppositories (for example, rectal suppositories, vaginal suppositories), small pills, nasal preparations, pulmonary preparations (inhalations), eye drops, etc., oral or parenteral preparations (for example, through intravenous, intramuscular, subcutaneous, intra-organ, intranasal, intradermal, instillation, intracerebral, intrarectal and other dosage forms, the drug is given to the vicinity of a tumor and directly given to the lesion). Preferably, the pharmaceutical composition is an injection.

The pharmaceutically acceptable excipient of the present invention is preferably a pharmaceutically acceptable injectable excipient, such as an isotonic sterile salt solution (sodium dihydrogen phosphate, disodium hydrogen phosphate, sodium chloride, potassium chloride, calcium chloride, magnesium chloride, or the like, or a mixture of the above salts). Or the pharmaceutical composition is dry, for example, a freeze-dried composition which may be suitably formed into an injectable solute by adding sterile water or normal saline.

A fourth aspect of the present invention provides the use of the CAR or the CAR-expressing cell of the present invention in prevention and/or treatment of a tumor highly expressing Robo1.

A fifth aspect of the present invention provides the use of the CAR or the CAR-expressing cell of the present invention in a medicament for preventing and/or treating a tumor highly expressing Robo1.

The tumor highly expressing Robo1 of the present invention includes breast cancer, liver cancer, lung cancer, pancreatic cancer, cervical cancer, ovarian cancer, rectal cancer, gastric cancer, colon cancer, prostate cancer, glioma, and the like.

The present invention adopts Slit2D2 to construct a CAR (Slit2D2-CAR), and uses it to modify and engineer cells, in particular, uses Slit2D2-CAR to modify and engineer T cells to construct Slit2D2-CART cells, and uses the Robo1 molecule as a target antigen, kills tumor cells by using Slit2D2-CART cells, which may be used as a cell drug for the treatment of tumor diseases. By using the CAR of the present invention, the engineered cells, especially T cells, can specifically recognize and kill tumors, and have higher tumoricidal activity.

DETAILED DESCRIPTION OF THE INVENTION

Figure 1:
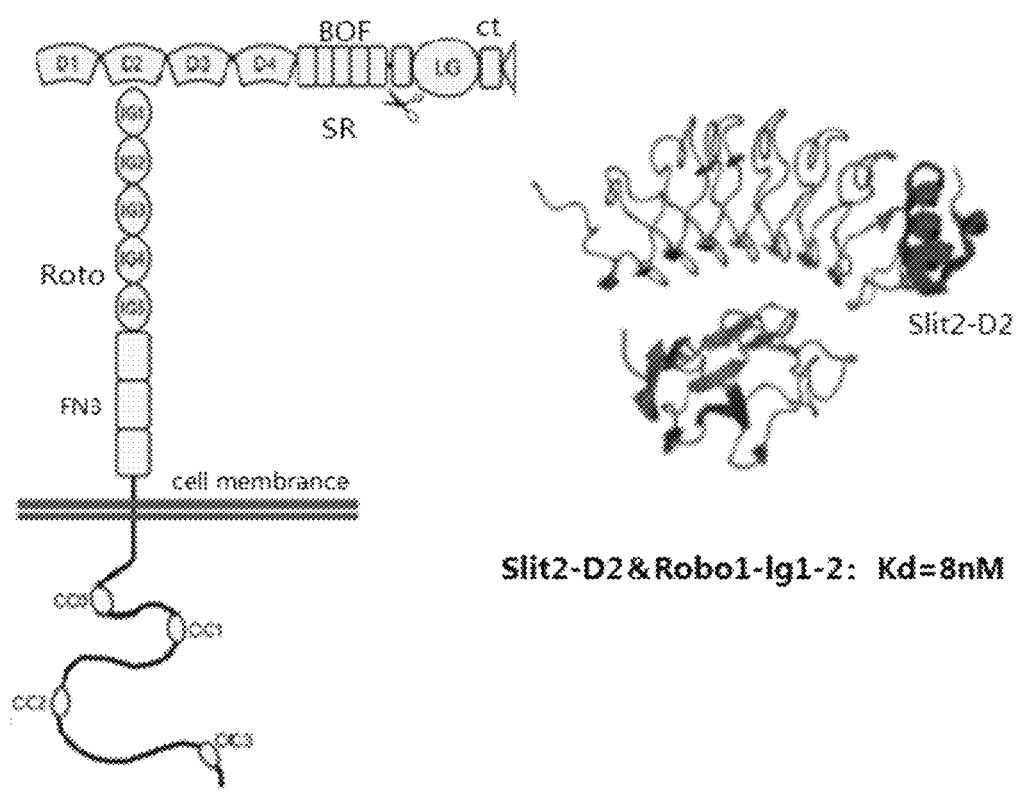
FIG. 1 is a schematic diagram showing the tertiary structure analysis of Slit2/Robo1 interaction region.
Figure 2:
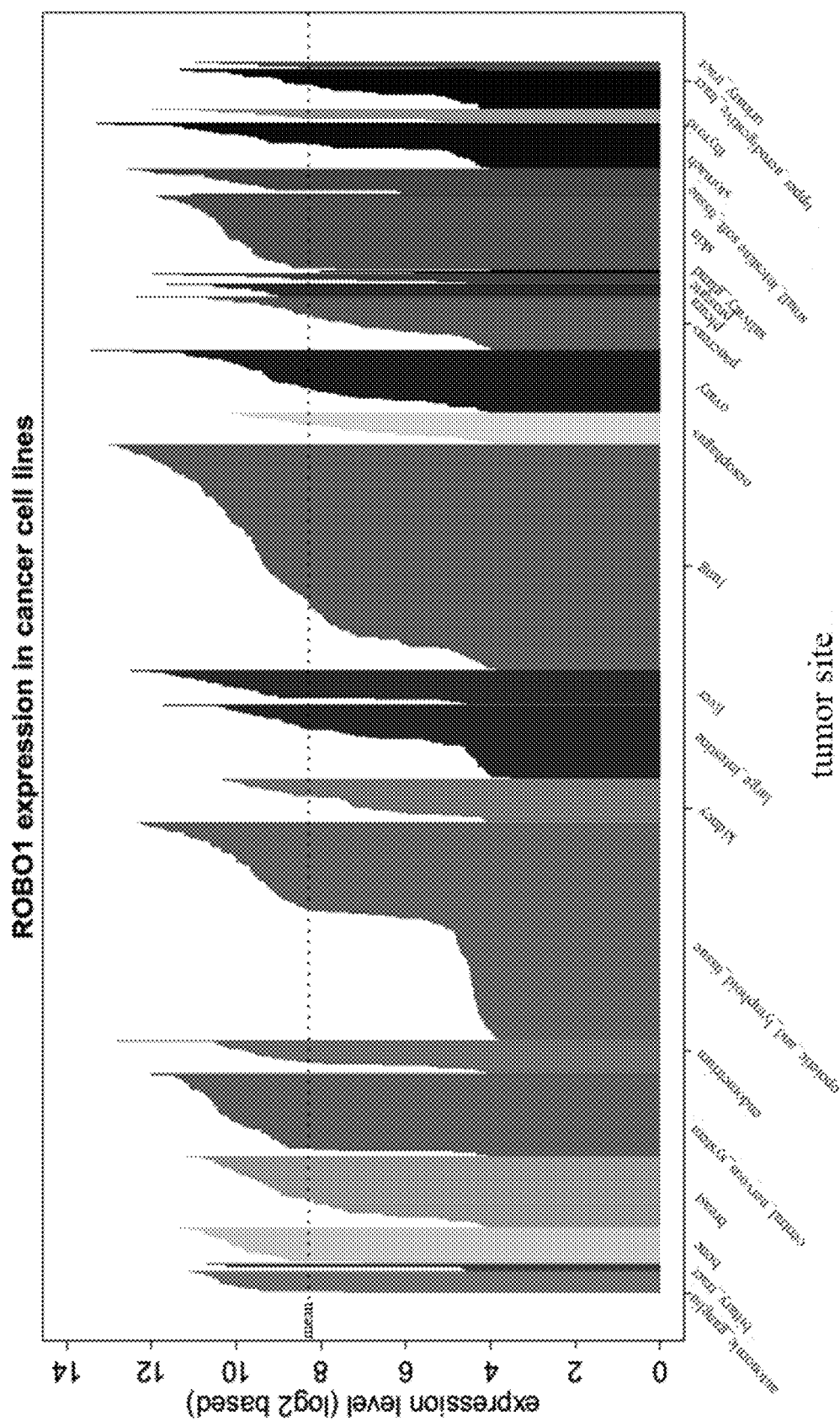
FIG. 2 shows the expression analysis of the Robo1 gene in tumor cells.
Figure 3:
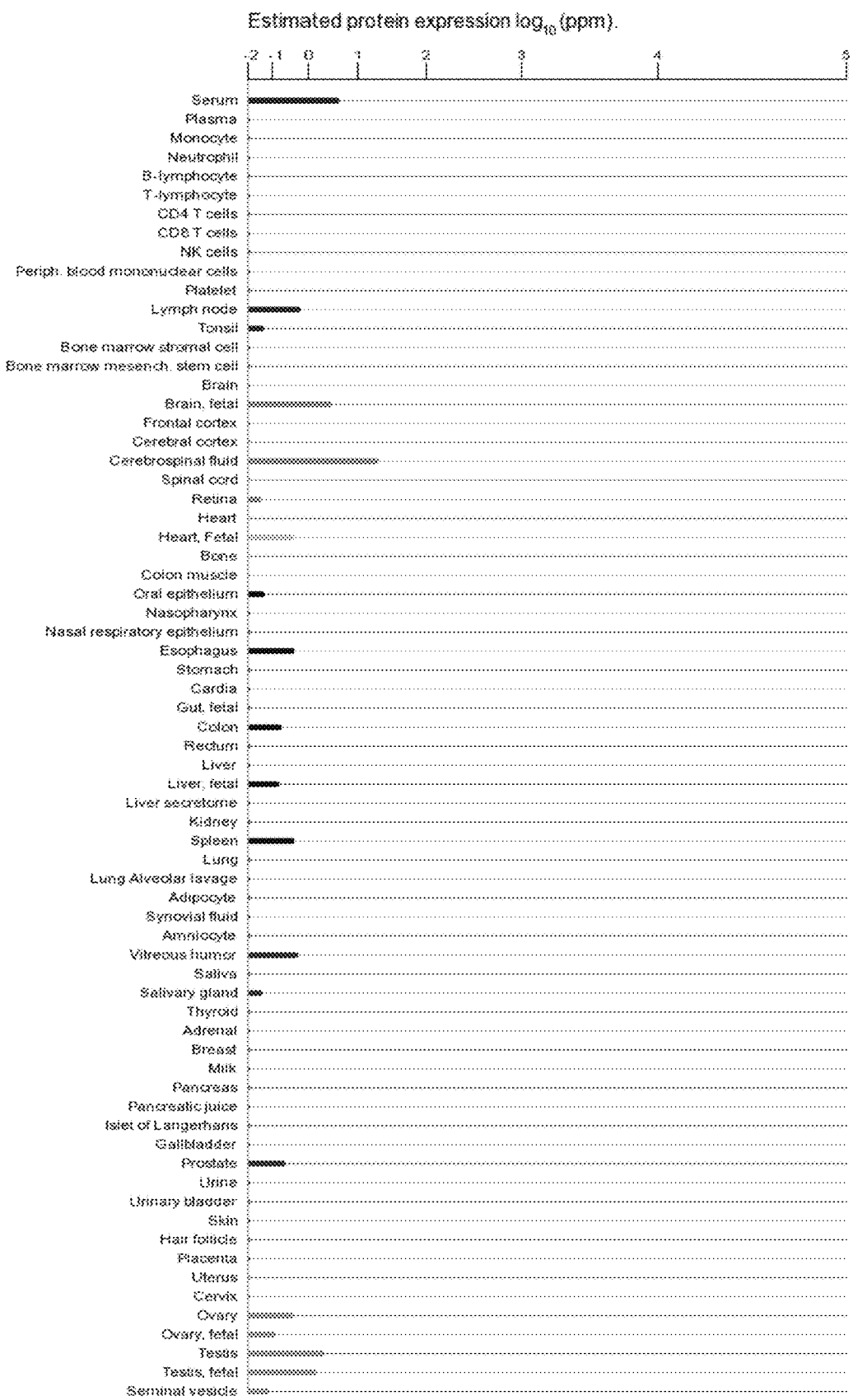
FIG. 3 shows the expression analysis of the Robo1 gene in tissues.

The term "chimeric antigen receptor (CAR)" as used in the present invention refers to a fusion protein comprising an extracellular domain capable of binding to an antigen, a transmembrane domain and an intracellular immune costimulator molecule, and "chimeric antigen receptor (CAR)" is also known as "chimeric receptor", "T-body" or "chimeric immunoreceptor (CIR)". "Extracellular domain capable of binding to an antigen" refers to any oligopeptide or polypeptide capable of binding to a specific antigen. "Transmembrane domain" refers to a polypeptide derived from any membrane-binding protein or transmembrane protein, or a synthetic polypeptide mainly comprising hydrophobic residues such as leucine and valine. "Intracellular immune costimulator molecule" refers to any oligopeptide or polypeptide known to function in a cell as a transmitting signal to cause activation or inhibition of a biological process.

The term "domain" as used in the present invention refers to a region having a specific structure and an independent function in a biological macromolecule, for example, the D2 domain of Slit2 protein refers to the second domain of the four leucine-rich repeats of the Slit2 protein.

The term "Slit2 protein" as used in the present invention refers to a neurotransmitter, which is an evolutionarily highly conserved secreted extracellular matrix glycoprotein having a molecular weight of about 200 kD, and plays a guiding role in axon growth and neuronal migration, and its structure consists of a signal peptide secreted extracellularly at the N-terminal, four leucine-rich repeats (LRRs), also designated as D1-D4 domains, a plurality of epidermal growth factor (EGF)-like repeats (7 in *Drosophila melanogaster*, and 9 in vertebrates), a laminin G-like domain and a cysteine-rich C-terminal domain.

The term "Robo1" as used in the present invention is a single-channel transmembrane receptor protein which is a receptor for Slit protein, and its extracellular region comprises five immunoglobulin conserved regions and three fibronectin type III repeats, and the intracellular region comprises four conserved regions: CC0, CC1, CC2 and CC3.

The terms "prevention", "preventing" or "treatment", "treating" as used in the present invention include therapeutic or prophylactic treatments or measures with the goal of preventing or slowing down a targeted pathological condition or illness. A subject is successfully "prevented" or "treated" if the subject exhibits a decrease or disappearance of one or more signs and symptoms of a particular disease that is observable and/or measurable after receiving a therapeutic amount of the fusion protein of the present invention according to the method of the present invention.

The contents of the present invention can be explained in more detail by the examples provided below. However, the content of the present invention is not limited to the contents set forth in the following examples.

Example 1 Preparation of Lentiviral Expression Vector

1. According to the known Slit2 sequence [GenBank: EAW92793.1], the second domain of Slit2, Slit2D2 (Hohenester2008), was designed and constructed. The known human CD8-TM transmembrane domain gene sequence, human 4-1BB intracellular domain gene sequence and CD3ζ intracellular domain gene sequence were searched from the GenBank database. The sequence of each gene is shown in SEQ ID NO: 6-9 of the Sequence Listing.

2. The above gene sequences were sequentially ligated in the order of the human Slit2D2 gene, CD8-TM membrane domain gene, human 4-1BB intracellular domain gene and CD3ζ intracellular domain gene, and different enzyme cleavage sites were introduced at each sequence junction to form complete gene sequence information of Slit2D2-CD8-TM-4-1BB-CD3ζ (Slit2D2-CAR), the sequence of which is shown in SEQ ID NO: 10 of the Sequence Listing.

Figure 4:
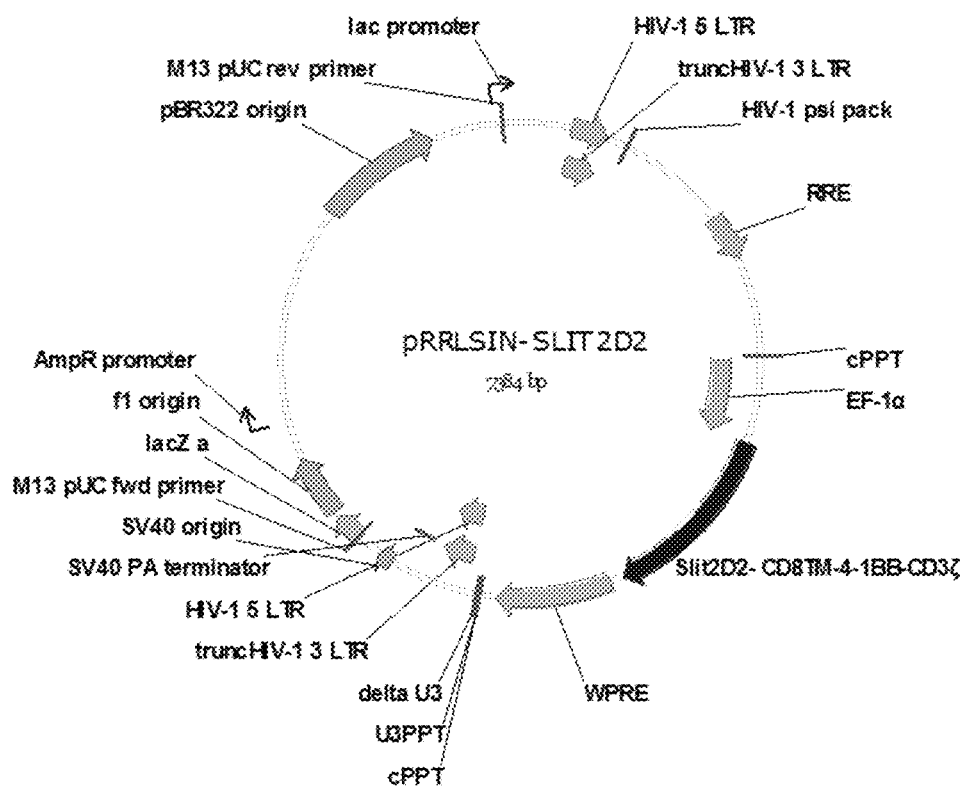
FIG. 4 is a schematic diagram of the pRRSLIN-Slit2D2 lentiviral expression vector of the present invention.

3. The gene sequence of Slit2D2-CD8-TM-4-1BB-CD3ζ was ligated into a pRRSLIN vector by enzymatic transformation, and the upstream of the gene was an EP-1a promoter. The vector was transformed into Stbl3 *Escherichia coli* strain, then transferred to solid medium containing ampicillin for propagation, and screened to obtain positive clones. The plasmid was extracted therefrom, and was digested to identify the clone. The vector was confirmed to be successfully constructed by sequencing, and a pRRSLIN-Slit2D2 lentiviral expression vector was obtained. The schematic diagram of the construction of the lentiviral expression vector is shown in FIG. 4.

Example 2 Preparation of Lentivirus 1. 24 hours prior to transfection, 293T cells were inoculated into a 15 cm culture dish at approximately $8 \times 10^6$ per dish. It was ensured that the cells were at a confluence of about 80% and evenly distributed in the culture dish at the time of transfection.
2. Preparation of solution A and solution B
Solution A: 6.25 mL 2×HEPES buffer (the amount of 5 large dishes packaged together worked best).
Solution B: A mixture with the following plasmids separately added: 112.5 μg of pRRLSIN-EF-PD1 (target plasmid); 39.5 μg of pMD2.G (VSV-G envelop); 73 μg of pCMVR8.74 (gag, pol, tat, rev); and 625 μL of 2M calcium ion solution. Total volume of solution B: 6.25 mL.
3. The solution B was thoroughly mixed, and while gently vortexing the solution A, the solution B was added dropwise, and allowed to stand for 5-15 minutes. The above mixed solution of A and B was gently vortexed, and added dropwise to the culture dish containing 293T cells. The culture dish was gently shaken back and forth to evenly distribute the mixture of DNA and calcium ions (the culture dish should not be rotated), and placed in an incubator and cultured for 16-18 hours.

A fresh culture medium was replaced, and the culture was continued. The lentivirus-containing supernatant was collected after 48 hours and 72 hours, respectively. It was observed that more than 95% of the cells showed green fluorescence through a fluorescence microscopy.

The above culture fluid was centrifuged at 500 g for 10 min at 25° C., and filtered using a PES membrane (0.45 μm). A centrifuge tube (Blechman Coulter ultra-clear SW28 centrifuge tube) was sterilized with 70% ethanol, and sterilized under a UV light for 30 min. The filtered lentivirus-containing supernatant was transferred to the centrifuge tube. A layer of 20% sucrose was carefully placed on the bottom of the tube (1 mL of sucrose was added per 8 mL of the supernatant). The tube was equilibrated with PBS, centrifuged at 25,000 rpm (82,700 g) for 2 h at 4° C. The centrifuge tube was carefully taken out, the supernatant was decanted, and the centrifuge tube was inverted to remove residual liquid. The centrifuge tube was added with 100 μL of PBS, sealed, placed at 4° C. for 2 h, gently vortexed every 20 min, centrifuged at 500 g for 1 min (25° C.). The lentivirus-containing supernatant was collected, cooled on ice, and then stored at −80° C.

Example 3 Preparation of Slit2D2-CART Cells 1. 0.5 mL of blood was subjected to a rapid pathogenic microbial detection to exclude infections of microorganisms such as HBV, HCV, HDV and HEV, HIV-1/2, *Treponema pallidum* and parasites, etc. Under aseptic conditions, 50 mL of blood was collected into a heparin bottle (anticoagulated with heparin) and immediately sent (4° C., within 24 hours) to the cell preparation laboratory to ensure that this process was free of pathogenic microbial contamination. After obtaining the patient's blood, in the GMP preparation room, the surface of the heparin bottle was wiped with an alcohol cotton ball for disinfection, which was then placed in a biosafety cabinet.

2. Two 50 mL centrifuge tubes were pre-opened, the blood was transferred to the two 50 mL centrifuge tubes, which were then tightened. The above two 50 mL centrifuge tubes filled with blood were centrifuged at 400 g (2000 rpm) for 10 min at room temperature in a centrifuge, and then the upper plasma was collected to leave a sediment layer. The collected autologous plasma was inactivated at 56° C. for 30 min, placed at 4° C. for 15 min, and centrifuged at 900 g for 30 min (4° C.). The supernatant was taken for use.
3. The above enriched blood cells were diluted with normal saline to 30 mL/tube. Two new 50 mL centrifuge tubes were opened, and each was added with 15 mL of human lymphocyte separation medium. The diluted blood cell fluid was slowly added to the centrifuge tubes containing the human lymphatic separation medium by a pipette, and then the centrifuge tubes were tightened. The blood was taken care of to be added to the upper layer of the lymphatic separation medium, and did not break the interface of the human lymphatic separation medium. The added blood cell fluid was placed in a centrifuge, which was adjusted to a minimum rate of rise and fall, and centrifuged at 400 g (2000 rpm) for 20 min (normal temperature). The middle leukocyte layer in the two tubes was collected into a 15 mL sterile centrifuge tube, added with 5 mL of normal saline, and washed twice (centrifuged at 400 g for 10 min) to obtain peripheral blood mononuclear cells (PBMC).
4. A complete growth medium was prepared. V-VIVO15 was added with autologous AB (FBS) to a concentration of 5%, and interleukin-2 (IL-2) to a concentration of 40 ng/mL. The isolated PBMC was diluted to $2 \times 10^6$/mL with the medium, 50 μL of which was taken for flow cytometry to detect the purity of T cells in PBMC.
5. On day 0, a buffer was prepared (1% fetal bovine serum (FBS) was added to a PBS buffer). Microbeads were selected as the cell culture carrier, which were shaken for 30 s or manually shaken up and down for 5 min. CD3/CD28 microbeads were placed in a 1.5 mL EP tube according to an amount ratio of microbeads to T cells of 3:1. 1 mL of buffer was added to wash the microbeads, and then a magnet was used to suck the microbeads from the EP tube outward for 1 min, then the wash solution was discarded, and the above procedure was repeated twice. Then, the microbeads were resuspended with the medium to the original volume. The cells and microbeads were mixed and added to a suitable culture flask at $2 \times 10^6$ PBMC/mL.
6. On day 2, the cell density was adjusted to $3-5 \times 10^6$/mL. The pRRSLIN-Slit2D2 lentiviral expression vector prepared in Example 1 was added at a ratio of lentiviral vector to cells of 1:5, at the same time, 4 μg/mL polybrene and 40 ng/mL IL-2 were added. After 4 h, fresh complete growth medium was supplemented to adjust the cell density to $1 \times 10^6$/mL to continue the culture. All the cells were centrifuged, and added with fresh medium to continue the culture.
7. Half volume medium was changed every 2-3 days to maintain a cell density of $0.5-1 \times 10^6$/mL.
8. On day 10-12, when the number of cells reached a level of $10^9$, the culture fluid was centrifuged at 400 g for 5 min to obtain immune cells, which was washed twice with pre-cooled PBS (400 g, 5 min).
9. Counting was performed with a blood counting chamber, and the cell group and the CART cell ratio were measured by flow cytometry. The color change of the medium, cell density, and cell morphology were observed daily and recorded accordingly. In the progressive enlarge cultivation process, the interleukin-2 required for the total volume was added.

Example 4: Construction and Detection of Engineered Cell Lines

Figure 5:
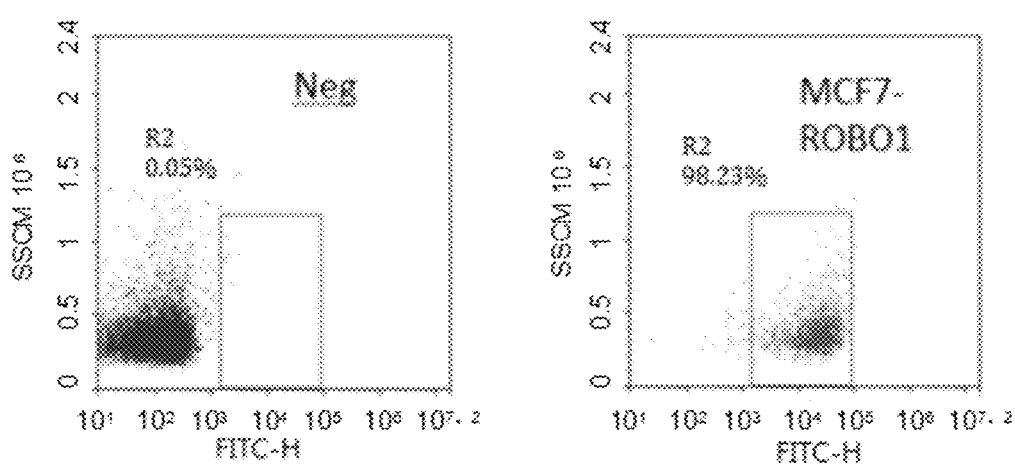
FIG. 5 is a diagram showing the flow cytometry results of the engineered cell line MCF7/ROBO1 highly expressing Robo1 in the present invention.

1. Preparation of lentivirus for constructing an engineered cell line highly expressing Robo1 (the specific preparation method was as the method in Example 2).
2. Infection of human breast cancer (MCF7) cells: one day before infection, $5\times10^5$ MCF7 cells were inoculated in a 6-well plate. When the cells grew to 80% on the next day, 500 μL of packaged PD-L1 virus was added to the 6-well plate, and control cells were set up (no lentivirus was added). After 12-16 hours, the medium was changed. 3 days after infection, Robo1-positive cells were sorted by flow cytometry.
3. Detection of engineered cell lines: $2\times10^5$ sorted Robo1-positive cells were taken, centrifuged at 400 g for 5 min, washed twice with pre-cooled PBS, and added with 2.5 μL of an antibody to Robo1 (Biolegend). The mixture was incubated for 20 min in the dark, centrifuged, and washed once with pre-cooled PBS. The cells were resuspended with 100 μL of PBS. The expression of Robo1 was detected by flow cytometry. The detection results are shown in FIG. 5. The experimental results showed that the engineered cell line was successfully constructed and could be used as a target cell for subsequent killing experiments.

Example 5 In Vitro Activity Assay of Slit2D2-CART Cells

The killing effects of Slit2D2-CART cells on the engineered cell line MCF-1/ROBO1 and the high Robo1-expressing hepatoma cell line SMCC7721 were detected by LDH release method, and LDH release was detected by ELISA.

1. Using RPMI-1640 medium containing 5% calf serum, the target cells were adjusted to $5\times10^4$/mL.
2. The target cells were added to a 96-well cell culture plate, at 100 μL per well. Three wells were used as natural release control wells of the effector cells (Slit2D2-CART cells), in which no target cells were added and only 100 μL of medium was added.
3. 100 μL of the effector cells were added to each well. The ratios of effector cells to target cells were 50:1; 25:1; 10:1; 5:1; and 1:1, respectively. The natural release wells were not added with the effector cells and only added with 100 μL of medium. The effector cells were incubated with the target cells for 6 hours. Three replicate wells were set for each experiment.
4. The largest release well (positive control) was added with 10 μL of Lysis Solution (10×), and incubated for 45 min-60 min. Three replicate wells were set for each experiment.
5. 50 μL of the sample to be tested and 50 μL of the control sample in the above steps 3 and 4 were taken separately, added to a fresh 96-well ELISA plate, which was then added with a reaction solution and a substrate, and protected from light for 30 min.
6. 50 μL of stop solution was added.
7. The optical density (OD value) of each well was measured on an ELISE reader with a detection wavelength of 490 nm or 492 nm. The measurement was completed within 1 hour.
8. Calculation of specific killing efficiency Killing rate=experimental group LDH (OD)/maximum LDH release group (OD).

Calculation formula: killing efficiency=(experimental group−effector natural release−target natural release)/(target maximum release−target natural release)×100%.

Figure 6:
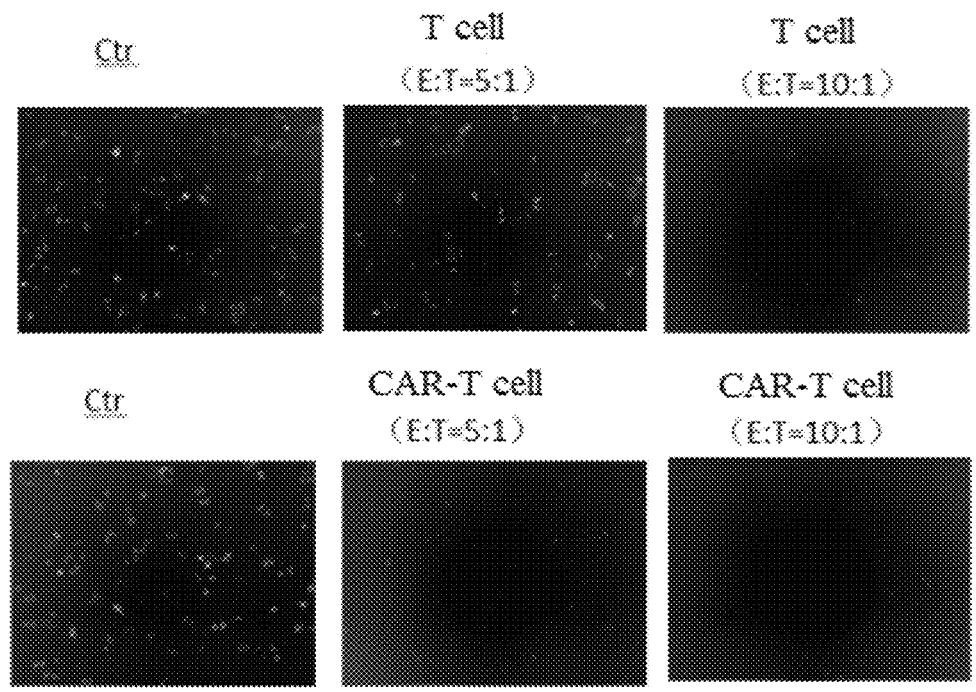
FIG. 6 shows a result of the in vitro killing experiments of the Slit2D2 CAR-T of the present invention.
Figure 7:
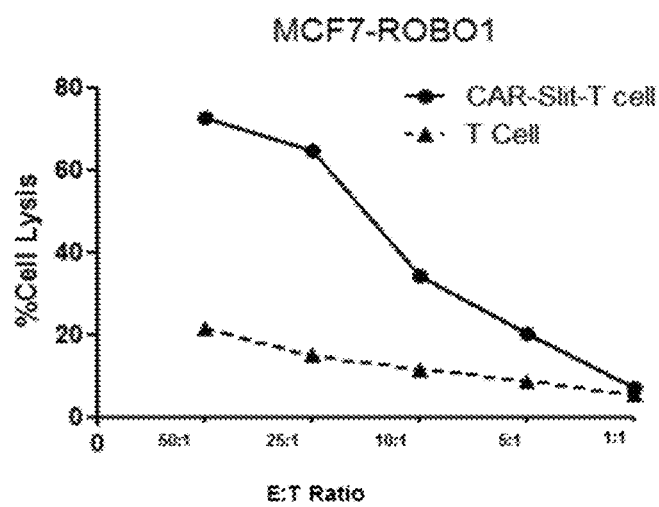
FIG. 7 is a diagram showing the in vitro killing effect of the Slit2D2 CAR-T cells on MCF-7/ROBO1 under different conditions of the ratio of effector cells to target cells in the present invention.
Figure 8:
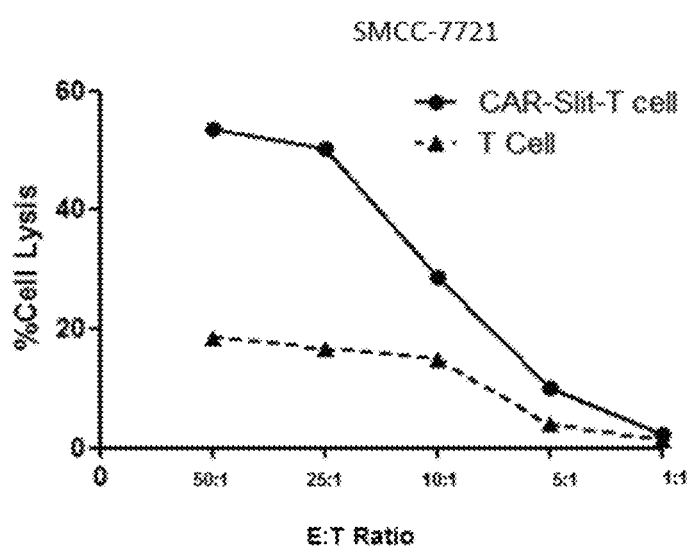
FIG. 8 is a diagram showing the in vitro killing effect of the Slit2D2 CAR-T cells on SMCC-7721 tumor cells under different conditions of the ratio of effector cells to target cells in the present invention.

The results of in vitro killing experiments of Slit2D2 CAR-T are shown in FIG. 6. The diagrams showing the in vitro killing effects of Slit2D2 CAR-T cells on MCF-7/ROBO1 and SMCC-7721 tumor cells under different conditions of the ratio of effector cells to target cells are shown in FIG. 7 and FIG. 8, respectively. The experimental results showed that the prepared Slit2D2 CAR-T cells could significantly kill the target cell lines MCF-7/Robo1 and SMCC7721 highly expressing Robo1. After 4 hours of co-incubation of the effector cells Slit2D2 CAR-T and the target cells with different ratios, the ELISA experiment results showed that as the ratio of effector cells:target cells increased, the cell killing efficiency also increased (see FIG. 7-8), and the microscopic imaging showed significant death of tumor cells (see FIG. 6).

---

The invention claimed is:

1. A chimeric antigen receptor consisting of the D2 domain of Slit2 protein, CD8 transmembrane domain, 4-1BB intracellular domain, and CD3ζ intracellular domain, referred to as Slit2D2-CD8TM-4-1BB-CD3ζ, wherein the Slit2D2-CD8TM-4-1BB-CD3ζ has the amino acid sequence of SEQ ID NO: 5.

2. A gene encoding the chimeric antigen receptor of claim 1, wherein the gene has the sequence of SEQ ID NO: 10.

3. A cell comprising the chimeric antigen receptor consisting of the D2 domain of Slit2 protein, CD8 transmembrane domain, 4-1BB intracellular domain, and CD3ζ intracellular domain, referred to as Slit2D2-CD8TM-4-1BB-CD3ζ, of claim 1.

4. The chimeric antigen receptor-expressing cell of claim 3, wherein the cell is a T cell or a cell population containing T cells.

5. The chimeric antigen receptor-expressing cell of claim 4, wherein the T cell is a T cell derived from human peripheral blood.

6. The chimeric antigen receptor-expressing cell of claim 3, wherein the D2 domain of Slit2 protein is expressed on the cell surface.

7. The chimeric antigen receptor-expressing cell of claim 3, wherein the chimeric antigen receptor-expressing cell is a T cell in which the gene encoding the Slit2D2-CD8-TM-4-1BB-CD3ζ is introduced, and the gene encoding the Slit2D2-CD8-TM-4-1BB-CD3ζ has the sequence of SEQ ID NO: 10.

8. A method for treating a tumor highly expressing Robo1, said method comprising: providing cells comprising the chimeric antigen receptor of claim 1 to a subject in need thereof.

* * * * *

SEQUENCE LISTING

```
<160> NUMBER OF SEQ ID NOS: 10

<210> SEQ ID NO 1
<211> LENGTH: 209
<212> TYPE: PRT
<213> ORGANISM: Artificial Sequence
<220> FEATURE:
<223> OTHER INFORMATION: D2 domain of Slit2 protein

<400> SEQUENCE: 1

Leu His Cys Pro Ala Ala Cys Thr Cys Ser Asn Asn Ile Val Asp Cys
1               5                   10                  15

Arg Gly Lys Gly Leu Thr Glu Ile Pro Thr Asn Leu Pro Glu Thr Ile
            20                  25                  30

Thr Glu Ile Arg Leu Glu Gln Asn Thr Ile Lys Val Ile Pro Pro Gly
        35                  40                  45

Ala Phe Ser Pro Tyr Lys Lys Leu Arg Arg Ile Asp Leu Ser Asn Asn
    50                  55                  60
```

-continued

```
Gln Ile Ser Glu Leu Ala Pro Asp Ala Phe Gln Gly Leu Arg Ser Leu
 65                  70                  75                  80

Asn Ser Leu Val Leu Tyr Gly Asn Lys Ile Thr Glu Leu Pro Lys Ser
                 85                  90                  95

Leu Phe Glu Gly Leu Phe Ser Leu Gln Leu Leu Leu Asn Ala Asn
            100                 105                 110

Lys Ile Asn Cys Leu Arg Val Asp Ala Phe Gln Asp Leu His Asn Leu
            115                 120                 125

Asn Leu Leu Ser Leu Tyr Asp Asn Lys Leu Gln Thr Ile Ala Lys Gly
        130                 135                 140

Thr Phe Ser Pro Leu Arg Ala Ile Gln Thr Met His Leu Ala Gln Asn
145                 150                 155                 160

Pro Phe Ile Cys Asp Cys His Leu Lys Trp Leu Ala Asp Tyr Leu His
                165                 170                 175

Thr Asn Pro Ile Glu Thr Ser Gly Ala Arg Cys Thr Ser Pro Arg Arg
            180                 185                 190

Leu Ala Asn Lys Arg Ile Gly Gln Ile Lys Ser Lys Lys Phe Arg Cys
        195                 200                 205

Ser

<210> SEQ ID NO 2
<211> LENGTH: 24
<212> TYPE: PRT
<213> ORGANISM: Artificial Sequence
<220> FEATURE:
<223> OTHER INFORMATION: CD8 transmembrane domain

<400> SEQUENCE: 2

Ile Tyr Ile Trp Ala Pro Leu Ala Gly Thr Cys Gly Val Leu Leu Leu
 1               5                  10                  15

Ser Leu Val Ile Thr Leu Tyr Cys
                 20

<210> SEQ ID NO 3
<211> LENGTH: 42
<212> TYPE: PRT
<213> ORGANISM: Artificial Sequence
<220> FEATURE:
<223> OTHER INFORMATION: 4-1BB intracellular domain

<400> SEQUENCE: 3

Lys Arg Gly Arg Lys Lys Leu Leu Tyr Ile Phe Lys Gln Pro Phe Met
 1               5                  10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40

<210> SEQ ID NO 4
<211> LENGTH: 112
<212> TYPE: PRT
<213> ORGANISM: Artificial Sequence
<220> FEATURE:
<223> OTHER INFORMATION: CD3?? intracellular domain

<400> SEQUENCE: 4

Arg Val Lys Phe Ser Arg Ser Ala Asp Ala Pro Ala Tyr Lys Gln Gly
 1               5                  10                  15

Gln Asn Gln Leu Tyr Asn Glu Leu Asn Leu Gly Arg Arg Glu Glu Tyr
                20                  25                  30
```

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
 50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 5
<211> LENGTH: 432
<212> TYPE: PRT
<213> ORGANISM: Artificial Sequence
<220> FEATURE:
<223> OTHER INFORMATION: Slit2D2-CD8TM-4-1BB-CD3??

<400> SEQUENCE: 5

Leu His Cys Pro Ala Ala Cys Thr Cys Ser Asn Asn Ile Val Asp Cys
 1               5                  10                  15

Arg Gly Lys Gly Leu Thr Glu Ile Pro Thr Asn Leu Pro Glu Thr Ile
                20                  25                  30

Thr Glu Ile Arg Leu Glu Gln Asn Thr Ile Lys Val Ile Pro Pro Gly
            35                  40                  45

Ala Phe Ser Pro Tyr Lys Lys Leu Arg Arg Ile Asp Leu Ser Asn Asn
 50                  55                  60

Gln Ile Ser Glu Leu Ala Pro Asp Ala Phe Gln Gly Leu Arg Ser Leu
 65                  70                  75                  80

Asn Ser Leu Val Leu Tyr Gly Asn Lys Ile Thr Glu Leu Pro Lys Ser
                85                  90                  95

Leu Phe Glu Gly Leu Phe Ser Leu Gln Leu Leu Leu Leu Asn Ala Asn
            100                 105                 110

Lys Ile Asn Cys Leu Arg Val Asp Ala Phe Gln Asp Leu His Asn Leu
            115                 120                 125

Asn Leu Leu Ser Leu Tyr Asp Asn Lys Leu Gln Thr Ile Ala Lys Gly
            130                 135                 140

Thr Phe Ser Pro Leu Arg Ala Ile Gln Thr Met His Leu Ala Gln Asn
145                 150                 155                 160

Pro Phe Ile Cys Asp Cys His Leu Lys Trp Leu Ala Asp Tyr Leu His
            165                 170                 175

Thr Asn Pro Ile Glu Thr Ser Gly Ala Arg Cys Thr Ser Pro Arg Arg
            180                 185                 190

Leu Ala Asn Lys Arg Ile Gly Gln Ile Lys Ser Lys Lys Phe Arg Cys
            195                 200                 205

Ser Thr Thr Thr Pro Ala Pro Arg Pro Pro Thr Pro Ala Pro Thr Ile
            210                 215                 220

Ala Ser Gln Pro Leu Ser Leu Arg Pro Glu Ala Cys Arg Pro Ala Ala
225                 230                 235                 240

Gly Gly Ala Val His Thr Arg Gly Leu Asp Phe Ala Cys Asp Ile Tyr
            245                 250                 255

Ile Trp Ala Pro Leu Ala Gly Thr Cys Gly Val Leu Leu Leu Ser Leu
            260                 265                 270

Val Ile Thr Leu Tyr Cys Lys Arg Gly Arg Lys Lys Leu Leu Tyr Ile
            275                 280                 285

-continued

```
Phe Lys Gln Pro Phe Met Arg Pro Val Gln Thr Thr Gln Glu Glu Asp
    290                 295                 300

Gly Cys Ser Cys Arg Phe Pro Glu Glu Glu Gly Gly Cys Glu Leu
305                 310                 315                 320

Arg Val Lys Phe Ser Arg Ser Ala Asp Ala Pro Ala Tyr Gln Gln Gly
                325                 330                 335

Gln Asn Gln Leu Tyr Asn Glu Leu Asn Leu Gly Arg Arg Glu Glu Tyr
            340                 345                 350

Asp Val Leu Asp Lys Arg Arg Gly Arg Asp Pro Glu Met Gly Gly Lys
        355                 360                 365

Pro Arg Arg Lys Asn Pro Gln Glu Gly Leu Tyr Asn Glu Leu Gln Lys
    370                 375                 380

Asp Lys Met Ala Glu Ala Tyr Ser Glu Ile Gly Met Lys Gly Glu Arg
385                 390                 395                 400

Arg Arg Gly Lys Gly His Asp Gly Leu Tyr Gln Gly Leu Ser Thr Ala
                405                 410                 415

Thr Lys Asp Thr Tyr Asp Ala Leu His Met Gln Ala Leu Pro Pro Arg
            420                 425                 430

<210> SEQ ID NO 6
<211> LENGTH: 627
<212> TYPE: DNA
<213> ORGANISM: Artificial Sequence
<220> FEATURE:
<223> OTHER INFORMATION: Nucleic acid encoding D2 domain of Slit2
      protein

<400> SEQUENCE: 6
ttgcactgcc ctgccgcctg tacctgtagc aacaatatcg tagactgtcg tgggaaaggt    60
ctcactgaga tccccacaaa tcttccagag accatcacag aaatacgttt ggaacagaac   120
acaatcaaag tcatccctcc tggagctttc tcaccatata aaagcttag acgaattgac    180 ctgagcaata atcagatctc tgaacttgca ccagatgctt tccaaggact acgctctctg   240
aattcacttg tcctctatgg aaataaaatc acagaactcc ccaaaagttt atttgaagga   300
ctgttttcct tacagctcct attattgaat gccaacaaga taaactgcct tcgggtagat   360
gcttttcagg atctccacaa cttgaacctt ctctccctat atgacaacaa gcttcagacc   420
atcgccaagg ggaccttttc acctcttcgg gccattcaaa ctatgcattt ggcccagaac   480
ccctttattt gtgactgcca tctcaagtgg ctagcggatt atctccatac caacccgatt   540
gagaccagtg gtgcccgttg caccagcccc cgccgcctgg caaacaaaag aattggacag   600
atcaaaagca agaaattccg ttgttca                                       627

<210> SEQ ID NO 7
<211> LENGTH: 72
<212> TYPE: DNA
<213> ORGANISM: Artificial Sequence
<220> FEATURE:
<223> OTHER INFORMATION: Nucleic acid encoding CD8 transmembrane domain

<400> SEQUENCE: 7
atctacatct gggcgccctt ggccgggact tgtggggtcc ttctcctgtc actggttatc    60 acccttttact gc                                                      72

<210> SEQ ID NO 8
<211> LENGTH: 126
<212> TYPE: DNA
```

```
<213> ORGANISM: Artificial Sequence
<220> FEATURE:
<223> OTHER INFORMATION: Nucleic acid encoding 4-1BB intracellular
      domain

<400> SEQUENCE: 8
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                             126

<210> SEQ ID NO 9
<211> LENGTH: 336
<212> TYPE: DNA
<213> ORGANISM: Artificial Sequence
<220> FEATURE:
<223> OTHER INFORMATION: Nucleic acid encoding CD3?? intracellular
      domain

<400> SEQUENCE: 9
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatgggggg aaagccgaga aggaagaacc ctcaggaagg cctgtacaat   180
gaactgcaga agataagat ggcggaggcc tacagtgaga ttgggatgaa aggcgagcgc   240
cggaggggca aggggcacga tggcctttac caggtctca gtacagccac caaggacacc   300
tacgacgccc ttcacatgca ggccctgccc ctcgc                             336

<210> SEQ ID NO 10
<211> LENGTH: 1296
<212> TYPE: DNA
<213> ORGANISM: Artificial Sequence
<220> FEATURE:
<223> OTHER INFORMATION: Nucleic acid encoding Slit2D2-CD8TM-4-1BB-CD3??

<400> SEQUENCE: 10
ttgcactgcc ctgccgcctg tacctgtagc aacaatatcg tagactgtcg tgggaaaggt    60
ctcactgaga tccccacaaa tcttccagag accatcacag aaatacgttt ggaacagaac   120
acaatcaaag tcatccctcc tggagctttc tcaccatata aaaagcttag acgaattgac   180
ctgagcaata atcagatctc tgaacttgca ccagatgctt tccaaggact acgtctctg   240 aattcacttg tcctctatgg aaataaaatc acagaactcc ccaaaagttt atttgaagga   300
ctgttttcct acagctcct attattgaat gccaacaaga taaactgcct tcgggtagat   360
gcttttcagg atctccacaa cttgaaccct ctctccctat atgacaacaa gcttcagacc   420
atcgccaagg gacctttc acctcttcgg gccattcaaa ctatgcattt ggcccagaac   480
cccttatttt gtgactgcca tctcaagtgg ctagcggatt atctccatac caacccgatt   540
gagaccagtg tgcccgttg caccagcccc cgccgcctgg caaacaaaag aattggacag   600
atcaaaagca gaaattccg ttgttcaacc acgacgccca cgccgcgacc accaacaccg   660
gcgcccacca tcgcgtcgca gcccctgtcc ctgcgcccag aggcgtgccg gccagcggcg   720
gggggcgcag tgcacacgag ggggctggac ttcgcctgtg atatctacat ctgggcgccc   780
ttggccggga cttgtggggt ccttctcctg tcactggtta tcaccctta ctgcaaacgg   840 ggcagaaaga aactcctgta tatattcaaa caaccattta tgagaccagt acaaactact   900
caagaggaag atggctgtag ctgccgattt ccagaagaag aagaaggagg atgtgaactg   960
agagtgaagt tcagcaggag cgcagacgcc cccgcgtacc agcagggcca gaaccagctc  1020
```

```
tataacgagc tcaatctagg acgaagagag gagtacgatg ttttggacaa gagacgtggc    1080
cgggaccctg agatgggggg aaagccgaga aggaagaacc ctcaggaagg cctgtacaat    1140
gaactgcaga aagataagat ggcggaggcc tacagtgaga ttgggatgaa aggcgagcgc    1200
cggaggggca aggggcacga tggcctttac cagggtctca gtacagccac caaggacacc    1260
tacgacgccc ttcacatgca ggccctgccc cctcgc                             1296
```